United States Patent [19]

Claussen

[11] 3,947,412

[45] Mar. 30, 1976

[54] PROCESS FOR THE MANUFACTURE OF 2-ARYL-VIC-TRIAZOLES

[75] Inventor: Uwe Claussen, Leverkusen, Germany

[73] Assignee: Bayer Aktiengesellschaft, Leverkusen, Germany

[22] Filed: Nov. 6, 1973

[21] Appl. No.: 413,208

[30] Foreign Application Priority Data
Nov. 6, 1972   Germany............................ 2254300
Aug. 1, 1973   Germany............................ 2338881

[52] U.S. Cl. ....................... 260/240 C; 260/308 A
[51] Int. Cl.² ...................................... C07D 249/16
[58] Field of Search ................... 260/308 A, 240 C

[56] References Cited
UNITED STATES PATENTS
3,666,758   5/1972   Dorlars et al. ................... 260/308 R OTHER PUBLICATIONS
Benson et al., Chem. Reviews, Vol. 46, pp. 20–22, (1950).

Primary Examiner—Paul M. Coughlan, Jr.
Attorney, Agent, or Firm—Plumley and Tyner

[57] ABSTRACT

Vic-triazoles are obtained in almost quantitative yield and high purity when α-oximino-arylhydrazones of the formula

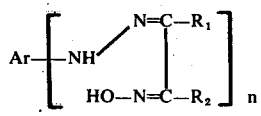

in which Ar represents an aromatic-carbocyclic or aromatic heterocyclic radical, $R_1$ denotes an aliphatic or aromatic radical, $R_2$ denotes hydrogen or an aliphatic or aromatic radical and $n$ denotes the numbers 1 or 2, are reacted with at least 1 mol equivalent of a cyclising agent in the presence of heavy metals or of their ions.

3 Claims, No Drawings

PROCESS FOR THE MANUFACTURE OF 2-ARYL-VIC-TRIAZOLES

It is known to prepare 2-aryl-vic-triazoles by cyclisation of α-oximinoarylhydrazones (Chem. Reviews 46, 1–68 (1950). These cyclisations with, for example, phosphorus pentachloride, take place with low yields, up to at most 50% of theory. Obtaining the triazole formed from the reaction mixture in a pure form is hampered considerably by by-products which are in part resinous and coloured.

Attempts have been made to avoid this difficulty by cyclisation in a melt of urea (German Offenlegungsschrift (German Published Specification) No. 1,670,914). This process produces better yields which in most cases are between 60 and 70% of theory and in some cases even reach 85% of theory. The disadvantage of this method is that the scope for varying the reaction conditions is slight, so that only relatively few compounds can be manufactured by this method. The method fails, in particular, in the case of the cyclisation of oximinohydrazones derived from diketones.

It has now been found, surprisingly, that the vic-aryltriazoles are obtained in almost quantitative yield and high purity when α-oximino-arylhydroazones of the general formula I

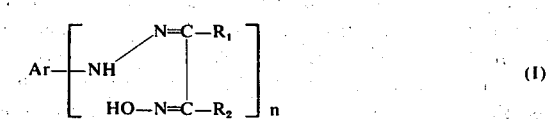

in which

Ar represents an aromatic-carbocyclic or aromatic heterocyclic radical, $R_1$ denotes an aliphatic or aromatic radical, $R_2$ denotes hydrogen or an aliphatic or aromatic radical and $n$ denotes the numbers 1 or 2, are reacted with at least 1 mol equivalent of a cyclising agent in the presence of heavy metals or of their ions.

Suitable aromatic-carbocyclic and aromatic-heterocyclic radicals are those of the benzene, naphthalene, diphenyl, diphenylmethane, diphenylethane, stilbene, tolane, pyridine, triazole, imidazole, pyrazole, coumarin or carbostyril series, which can optionally contain further substituents, for example halogen atoms or alkyl, alkoxy, hydroxyl, nitrile, carboxyl, carbonamido, sulpho, alkylcarbonyl, alkoxycarbonyl, alkylsulphonyl or arylsulphonyl groups, alkyl and alkoxy groups preferably being understood as groups with 1–4 atoms. Suitable arylsulphonyl groups are phenylsulphonyl and tolylsulphonyl. Compounds of the formula I are known, for example, from German Offenlegungsschriften (German Published Specifications) Nos. 1,670,969, 1,670,999, 1,594,845, 1,962,353, 2,037,854, 2,040,189 and 1,917,740 and from British patent specifications Nos. 1,215,507, 1,108,416, 1,154,995 and 1,155,229.

A particularly distinct effect is found in the case of compounds in which

Ar represents the radical of a coumarin system, $R_1$ represents an alkyl group and $R_2$ represents an aryl group.

By the term heavy metals there are here preferably to be understood the transition metals, that is to say the elements of sub-group 1 and 8 of the periodic system of the elements. Of these, metallic copper and copper ions are particularly active.

By cyclising agents there are understood compounds which produce direct acylation and compounds which form an acylating agent under the reaction conditions.

The group of the direct acylating agents includes, for examples, acid anhydrides, isocyanates and acyl halides. Examples of compounds which only form an acylating agent under the reaction conditions are ureas and salts of cyanic acid and isocyanic acid.

Suitable acid anhydrides are those of the formula

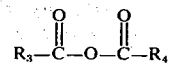

wherein $R_3$ and $R_4$ independently of one another represent an optionally substituted $C_1$–$C_4$-alkyl, $C_1$–$C_4$-alkoxy or phenyl radical.

Suitable isocyanates are those of the formula $$R_5-N=C=O$$

wherein $R_5$ denotes hydrogen, $C_1$–$C_6$-alkyl, $C_5$–$C_7$-cycloalkyl, phenyl, phenylcarbonyl or phenylsulphonyl, it being possible for the individual groups to be substituted by halogen or $C_1$–$C_4$-alkyl, $C_1$–$C_4$-alkoxy or nitro groups.

Suitable acyl halides are those of the formula

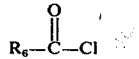

wherein $R_6$ represents an optionally substituted $C_1$–$C_6$-alkyl or phenyl radical or a $C_1$–$C_6$-alkylamino or phenyl-amino radical, it being possible for the phenyl radical to be substituted by $C_1$–$C_4$-alkyl or $C_1$–$C_4$-alkoxy groups or halogen atoms. Suitable ureas are those of the formula

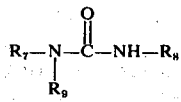

wherein $R_7$, $R_8$ and $R_9$ independently of one another represent hydrogen or optionally substituted $C_1$–$C_4$-alkyl or phenyl radicals.

Suitable salts of isocyanic acid and cyanic acid are the alkali metal salts.

Particularly preferred cyclising agents are isocyanic acid, methyl isocyanate, ethyl isocyanate, methoxymethyl isocyanate, cyclohexyl isocyanate, phenyl isocyanate, tolyl isocyanate, nitrophenyl isocyanate, benzoyl isocyanate, phenyl-sulphonyl isocyanate, toluylene diisocyanate, pyrocarbonic acid methyl ester, pyrocarbonic acid ethyl ester, acetic anhydride, N,N'-diphenylurea, N,N'-dimethylurea, N,N-dimethyl-urea, monomethylurea and urea.

In carrying out the process according to the invention in practice, an appropriate procedure to follow is to add to the solution or suspension of the α-oximino-aryl-hydrazones of the formula I 0.01 to 5 mols, preferably 0.01 to 0.5 mol, of a transition metal or of a transition metal salt, relative to 1 mol of oximinohydrazone, and subsequently to add the cyclising agent in an amount of at least 1 mol, preferably 2 mols. The reaction can be carried out at temperatures between 0° and 150°C.

Examples of suitable solvents for the isocyanate or carbamide-acid halide variant are: formamide, dimethylformamide, dimethylacetamide, N-methylpyrrolidone, ε-caprolactam, pyridine, picolines, quinoline, triethylamine, dimethylbenzylamine and methoxypropionitrile.

When using the remaining cyclising agents it is also possible to employ other polar solvents, apart from the solvents mentioned, for example water, alcohols, glycols and their ethers as well as hydrocarbons, ethers, halogenated hydrocarbons and ketones. Xylene, chlorobenzene, dichlorobenzene, glycol monomethyl ether, cyclohexanone and glycol monomethyl ether acetate may be mentioned as examples.

The reaction velocity and the yield can be accelerated by addition of small amounts of alkaline compounds. For this purpose it is in particular possible to use the alkali metal hydroxides and alkali metal carbonates, which are employed in amounts of, preferably, 0.01 to 0.1 mol equivalent per mol of α-oximinoarylhydrazone of the formula I.

The 2-aryl-v-triazoles obtainable according to the process of the invention, which correspond to the formula

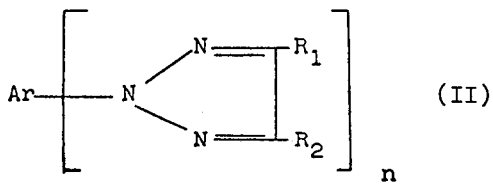

in which

Ar, $R_1$, $R_2$ and n have the abovementioned meaning are mostly known and are valuable optical brighteners, UV absorbers and intermediate products for brighteners and dye-stuffs.

Thus, for example, compounds of the formula (II), in which

Ar represents a stilbene, coumarin, naphthalimide and dibenzenethiophenedioxide radical are excellent optical brighteners (British patent specifications Nos. 1,108,416, 1,155,229, 1,154,995, 1,113,918 and 1,201,579 and U.S. Pat. specification 3,459,744).

Compounds in which Ar represents a p-tolyl radical ($n = 1$) or diphenyl-ethane radical ($n = 2$) can be converted into stilbene brighteners according to known processes (see, for example, U.S. Pat. No. 3,351,592 and French Pat. No. 1,480,699).

Aryltriazoles of the formula (II) which contain nitro groups can be converted according to processes which are in themselves known into corresponding aminoaryltriazoles which are valuable starting materials for the manufacture of azo dyestuffs (French Pat. No. 1,391,676 and 1,398,366).

2-Phenyl-4-methyl-v-triazole is an effective UV absorber (Chem. Abstr. 57, 8100 d).

EXAMPLE 1

158 g of N-(3-phenyl-coumarinyl-7)-α-oximinopropiophenonehydrazone are suspended in 800 ml of glycol monomethyl ether, 5 g of copper sulphate. 5 $H_2O$ and 100 g of urea are added and the mixture is heated for 15 hours at the reflux temperature (125°–130°C). The solid gradually dissolves, with slow evolution of ammonia and carbon dioxide. The mixture is then cooled to room temperature and the 3-phenyl-7-[2-(4-phenyl, 5-methyl)-1,2,3-triazolyl]-coumarin which has precipitated is filtered off, washed with methanol and dried. 146 g of crystals, corresponding to 96% of theory, are obtained, which after crystallisation from glycol monomethyl ether yield 114 g.

EXAMPLE 2

168 g of N-(3-phenyl-coumarinyl-7)-α-oximinopropiophenonehydrazone, of 95.8% purity, and 5 g of $CuSO_4 .6H_2O$ are suspended in 100 ml of pyridine. The mixture is warmed to 70°–80°C and 48 g of methyl isocyanate are added dropwise. The reaction mixture dissolves, with an exothermic reaction and vigorous evolution of $CO_2$ (about 10 liters of gas being evolved). The solvent is removed by steam distillation and the residue is crystallised from glycol monomethyl ether. The yield exceeds 95% of theory.

EXAMPLE 3

44 g of N-[3-(4-chloropyrazolyl-)coumarinyl-7]-α-oximinopropiophenonehydrazone are suspended in 100 ml of DMF and are heated under reflux with 170 ml of acetic anhydride and 10 g of sodium acetate in the presence of 20 g of $CuSO_4 . 5 H_2O$ for 3 hours. After cooling, the contents of the flask are diluted with an equal volume of water and the crystals which have precipitated are filtered off. After recrystallisation from glycol monomethyl ether, 3-(4-chloro-pyrazolyl-)7 -[2-(4-phenyl-5-methyl-)1,2,3-triazolyl]-coumarin is obtained in 80% yield in the form of pale yellow crystals.

Similar results are obtained on using N-(3-phenyl-coumarinyl-7)-α-oximino-(4-phenyl)-propiophenonehydrazone instead of the hydrazone mentioned in Example 3.

EXAMPLE 4

18 g of pyrocarbonic acid diethyl ester are added dropwise to a suspension of 41 g of N-(3-phenyl-coumarinyl-7)-α-oximinopropiophenonehydrazone and 3 g of $CuSO_4 . 5H_2O$ in 100 ml of DMF at 70°–80°C. The starting compound dissolves, with vigorous evolution of $CO_2$. After cooling, and diluting with an equal volume of water, 35 g of pale yellow crystals, representing 95% of theory, crystallise.

EXAMPLE 5

41 g of N-(3-phenyl-coumarinyl-7)-α-oximinopropiophenonehydrazone (95.8%) in 100 ml of pyridine are heated with 3 g of copper powder to 70°C. 13.5 g of methyl isocyanate are dropped into the suspension and react exothermically with evolution of $CO_2$, which at times is vigorous. As soon as the material has dissolved, the excess copper is filtered off hot and the mother liquor is stirred until cold. The crystals which have precipitated are filtered off and washed with methanol on the filter. 32 g of 3-phenyl-7-[2-(4-phenyl-5-methyl)-1,2,3-triazolyl]-coumarin are obtained as pale yellow crystals, representing 85% of theory.

EXAMPLE 6

397 g of the hydrazone from 3-phenyl-7-hydrazino-coumarin and α-oximinopropiophenone are suspended in 200 ml of glycol monomethyl ether and warmed with 20 g of potassium carbonate, 10 g of Cu powder and 250 g of urea to 125°–130°C. After boiling under reflux for 2-2½ hours, the contents of the flask dissolve and after refluxing for 4 hours they are cooled to 5°C. The crystals which have precipitated out are filtered off and washed with methanol, and after recrystallisation from glycol monomethyl ether, 285 g of 3-phenyl-7-[2-(4-phenyl-5-methyl)-1,2,3-triazolyl]-coumarin are obtained in the form of pale yellow crystals.

EXAMPLE 7

70.6 g of the disodium salt of 4,4'-bis-(α-oximinoacetophenonehydrazono)-stilbene-2,2'-disulphonic acid in 500 ml of diethylene glycol are heated with 100 g of urea and 2 g of Cu powder. The exothermic reaction commences at approx. 80°C and rapidly rises to 110°C. After 30 minutes, the evolution of gas has ceased. The mixture is stirred for a further hour at 110°C and is poured out onto 2 l of water and filtered. The crude paste is purified by dissolving it in 1,800 ml of boiling water and adding 100 ml of 40% strength sodium hydroxide solution, whereupon the sodium salt of 4,4'-bis-(4-phenyl-vic-triazolyl)-stilbene-2,2'-disulphonic acid is obtained as light yellow crystals. After drying, 65 g of cyclisation product are obtained; this gives a clear solution in water, having a light blue daylight fluorescence.

EXAMPLE 8

39.7 g of N-3-(phenyl-coumarinyl-7-)-α-oximinopropiophenonehydrazone are heated with 1 g of Cu powder and 20 g of urea in 100 ml of methoxypropionitrile. The substance dissolves in approx. 20 minutes at between 130° and 150°C, with the evolution of gas. The undissolved copper is filtered off hot and the filtrate is diluted with 200 ml of methanol; the precipitate is isolated, washed with methanol until the filtrate issues clear, and subsequently dried. 29.7 g of crude product are obtained, which after recrystallisation from 83% strength sulphuric acid give 29.4 g of pure 3-phenyl-7-[(4-methyl-5-phenyl-)1,2,3-triazolyl-(2)-]-coumarin.

If the procedure indicated in the preceding example is followed and instead of the Cu powder the catalysts indicated in column 1 are used, the yields shown in column 3 are obtained if no base is added, whilst column 2 shows the yields if 0.075 mol of (anhydrous) potassium carbonate is added per mol of hydrazone.

ether are then added and 800 ml of solvent are distilled off. For cyclisation, 140 g of urea and an approx. 1 mm thick Cu sheet weighing 162.3 g are added to the batch, which is now anhydrous, and the whole is heated to 126°–131°C. When solution has occurred, the batch is cooled and diluted with 500 ml of methanol and the precipitate is filtered off and washed with methanol and with hot water. 115 g of 3-phenyl-7-[(4-methyl-5-phenyl)-1,2,3-triazolyl(2)-]-coumarin are obtained. The decrease in weight of the Cu sheet is 0.6 g.

EXAMPLE 10

16.7 g of dimethylbenzylamine, 0.2 g of Cu powder and 70 g of N-(3-phenyl-coumarinyl-7)-α-oximinopropiophenone-hydrazone in 140 ml of glycol monomethyl ether acetate are treated dropwise, at 85°C, with 36 g of acetic anhydride, and the mixture is kept for 3 hours at this temperature, clarified with fuller's earth and cooled. After filtration and washing with methanol and water, 54 g of crystals are obtained. The same experiment without addition of Cu gives a yield of only 38 g.

I claim:

1. Process for the manufacture of 2-aryl-vic-triazoles which comprises reacting in the presence of copper or an ion of copper an α-oximino-arylhydrazone with a cyclizing agent wherein said aryl is a radical of the benzene, naphthalene, diphenyl, diphenylmethane, diphenylethane, stilbene, tolane, pyridine, triazole, imidazole, pyrazole, coumarin or carbostyril series and said cyclizing agent is selected from the group consisting of:

a. acid anhydride of the formula

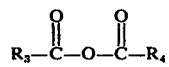

wherein $R_3$ and $R_4$, independently of each other are $C_1$–$C_4$-alkyl, $C_1$–$C_4$-alkoxy, or phenyl;

b. isocyanate of the formula

wherein $R_5$ is hydrogen, $C_1$–$C_6$-alkyl, $C_5$–$C_7$-cycloalkyl,

| | 1 | 2 | | 3 | |
|---|---|---|---|---|---|
| Catalyst | Amount in mol per mol of hydrazone | Yield, % | | Yield, % | |
| | | Crude | Pure | Crude | Pure |
| None | — | 81 | 54 | 50 | 41 |
| $CuSO_4 \cdot 5H_2O$ | 0.04 | 93 | 83.5 | 91 | 79 |
| CuCl | 0.10 | 89 | 78 | 86 | 74 |
| CuCN | 0.12 | 89 | 66 | 92 | 81 |
| Cu powder | 0.16 | 95 | 72.5 | 78.5 | 78 |
| Cu powder | 0.016 | 81 | 66 | — | — |
| $Cu + CuSO_4 \cdot 5H_2O$ | 0.08 + 0.02 | 93 | 77 | 93 | 82 |
| $NiCl_2 \cdot 6H_2O$ | 0.04 | 87 | 71 | 82 | 69 |
| $Cu + NiCl_2 \cdot 6H_2O$ | 0.016 + 0.001 | 87 | 59 | — | — |

EXAMPLE 9

920 ml of glycol monomethyl ether, 46 g of anhydrous sodium acetate, 128 g of oximinopropiophenone of 70.1% purity and 182 g of 3-phenyl-7-hydrazinocoumarin of 69.2% purity are introduced into a 2 l sulphonation beaker and warmed to 95°C for 2 hours. 30 g of $K_2CO_3$ and 500 ml of glycol monomethyl phenyl, phenylcarbonyl, phenylsulphonyl, $C_1$–$C_6$-alkyl substituted by $C_1$–$C_4$-alkoxy, or phenyl substituted by $C_1$–$C_4$-alkyl, $C_1$–$C_4$-alkoxy, or nitro;

c. acyl halide of the formula

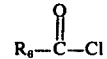

wherein $R_6$ is $C_1$–$C_6$-alkyl, phenyl, $C_1$–$C_6$-alkylamino, phenylamino, substituted phenyl, where the substituent is $C_1$–$C_4$-alkyl, $C_1$–$C_4$-alkoxy, or halogen;

d. urea of the formula

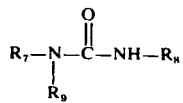

wherein $R_7$, $R_8$, and $R_9$, independently of each other are hydrogen, $C_1$–$C_4$-alkyl, or phenyl;

e. alkali metal salts of cyanic acid; and f. alkali metal salts of isocyanic acid.

2. Process of claim 1 wherein said cyclizing agent is isocyanic acid, methyl isocyanate, ethyl isocyanate, methoxymethyl isocyanate, cyclohexyl isocyanate, phenyl isocyanate, tolyl isocyanate, nitrophenyl isocyanate, benzoyl isocyanate, phenylsulphonyl isocyanate, toluylene diisocyanate, pyrocarbonic acid methyl ester, pyrocarbonic acid ethyl ester, acetic anhydride, N,N'-diphenylurea, N,N'-dimethylurea, monomethylurea, or urea.

3. Process of claim 1 employing 0.01 to 5 mols of α-oximinoarylhydrazone, 0.01 to 0.5 mols of copper, or an ion of copper per mol of α-oximino-arylhydrazone, and at least 1 mol of said cyclizing agent, at a reaction temperature of 0°–150°C.

* * * * *